United States Patent [19]
Folden

[11] Patent Number: 5,336,173
[45] Date of Patent: Aug. 9, 1994

[54] PERITONEAL DIALYSIS TUBING SET AND METHOD OF OPERATION

[75] Inventor: Thomas I. Folden, Alamo, Calif.

[73] Assignee: Fresenius USA, Inc., Walnut Creek, Calif.

[21] Appl. No.: 121,141

[22] Filed: Sep. 14, 1993

Related U.S. Application Data

[63] Continuation-in-part of Ser. No. 821,090, Jan. 16, 1992, Pat. No. 5,250,041, which is a continuation-in-part of Ser. No. 621,421, Nov. 30, 1990, abandoned.

[51] Int. Cl.$^5$ ................................................ A61M 1/00
[52] U.S. Cl. ........................................ 604/29; 604/28; 604/284
[58] Field of Search ............... 604/905, 280, 283, 284, 604/27, 28, 29, 49, 264, 4-6; 137/68 R

[56] References Cited

U.S. PATENT DOCUMENTS

| | | | |
|---|---|---|---|
| 4,239,041 | 12/1980 | Popovich et al. | 604/29 |
| 4,585,436 | 4/1986 | Davis et al. | 604/4 |
| 4,586,920 | 5/1986 | Peabody | 604/29 |
| 4,620,846 | 11/1986 | Goldberg et al. | 604/28 |
| 4,810,241 | 3/1989 | Rogers | 604/29 |
| 4,994,026 | 2/1991 | Fecondini | 604/29 |
| 5,141,492 | 8/1992 | Dadson et al. | 604/29 |
| 5,221,267 | 6/1993 | Folden | 604/905 |
| 5,250,041 | 10/1993 | Folden et al. | 604/905 |

*Primary Examiner*—C. Fred Rosenbaum
*Assistant Examiner*—Chalin Smith
*Attorney, Agent, or Firm*—Beaton & Swanson

[57] ABSTRACT

A tubing set for performing peritoneal dialysis and a method of operating the same. The tubing set includes elements for administering CCPD as well as elements for administering CAPD wherein preferably the CCPD and CAPD elements share a common reservoir bag and solution bags. The two sets of elements are separable by a releasable coupling. The CCPD elements may include multiple patient connectors in series to allow for multiple separate CCPD therapies. The solution bag and drain bag are separable from the other elements so that the empty solution bag from one tubing set can be used as the drain bag for the next tubing set.

19 Claims, 3 Drawing Sheets

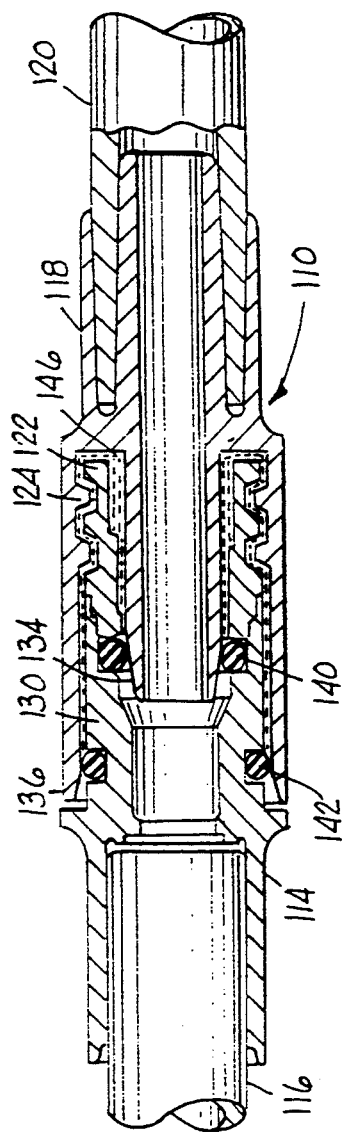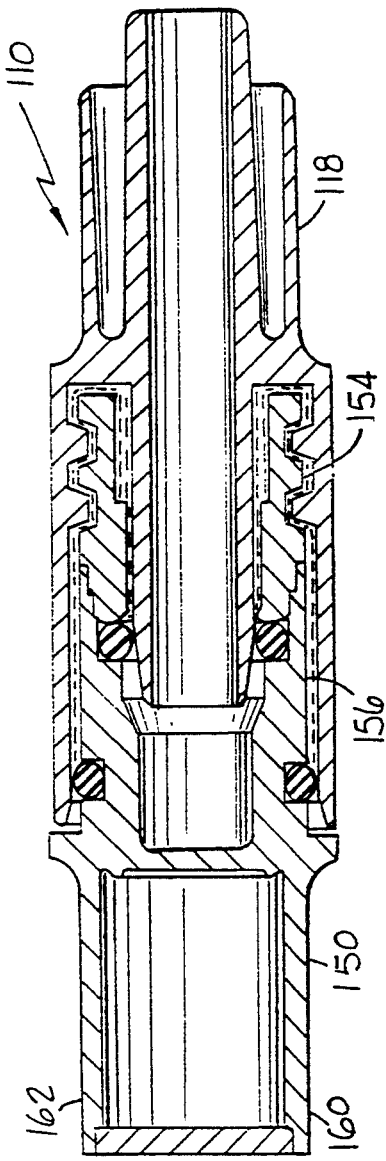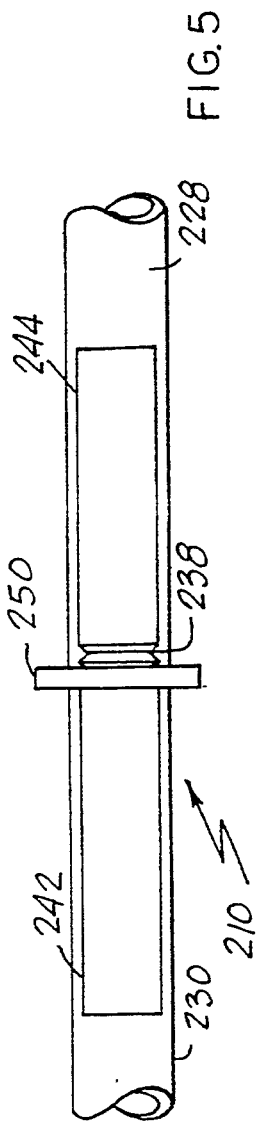

PERITONEAL DIALYSIS TUBING SET AND METHOD OF OPERATION

This application is a continuation-in-part of application Ser. No. 07/821,090 filed Jan. 16, 1992, now U.S. Pat. No. 5,250,041 which is a continuation-in-part of application Ser. No. 07/621,421 filed Nov. 30, 1990 now abandoned.

FIELD OF THE INVENTION

This invention relates to improved means for performing peritoneal dialysis. More specifically, the invention is directed at an extremely efficient and easy to use tubing set for Continuous Ambulatory Peritoneal Dialysis ("CAPD") and Continuous Cycling Peritoneal Dialysis ("CCPD") and a method of operating the same.

BACKGROUND OF THE INVENTION

There are two broad categories of techniques for the treatment of patients who have experienced significant renal failure. The traditional therapy has been hemodialysis, where the patient's blood is passed through filters that will remove the waste material from the patient's bloodstream. The second technique is peritoneal dialysis, where solutions are cycled into and out of the peritoneal cavity of the patient and wastes are removed with the spent solution.

Both techniques operate by the principles of diffusion across semipermeable membranes. In the case of peritoneal dialysis, the membrane that is used is the patient's peritoneal membrane. Although not as efficient as hemodialysis, peritoneal dialysis offers several advantages that have enhanced its desirability. For example, automated devices have been developed that allow a patient to undergo a dialysis treatment at night while the patient is asleep. Utilizing these automated devices allows the patient great mobility and freedom of time.

Peritoneal dialysis can be accomplished in several different modes. In Continuous Ambulatory Peritoneal Dialysis ("CAPD"), the infusion of solution into and out of the peritoneal cavity is accomplished while the patient functions normally throughout the day. The obvious disadvantages of CAPD are the cumbersome devices that must be worn by the patient. Examples of CAPD systems can be seen in U.S. Pat. Nos. 4,747,822 of Peabody and 4,620,846 of Goldberg, et al.

Two types of peritoneal dialysis therapies that are particularly suitable for use with automated systems are Intermittent Peritoneal Dialysis (IPD) and Continuous Cycling Peritoneal Dialysis ("CCPD"). In IPD, large amounts of dialysis solution (up to 40 liters) are cycled through the patient's peritoneal cavity over a 4 to 24 hour period. In CCPD, the dialysis treatment is more or less continuous, with dwell times of 3 to 4 hours at night, and then throughout the waking time of the patient a single dose of dialysis solution is retained within the patient. There are certain advantages to each of these two different therapy techniques.

In both IPD and CCPD an automated dialysis apparatus operates in generally the same manner. The dialysis solution and "tubing administration set" or simply "tubing set" is integrated with the valving, heating and control functions associated with the automated apparatus. In many of the systems, premeasured amounts of dialysis solution are either pumped or delivered by gravity flow to a heating station. At the heating station the solution is warmed to body temperature in order to prevent the uncomfortable sensation of introducing room temperature or cooler solution into the peritoneal cavity. The warmed solution is then allowed to enter the patient via a catheter implanted in the patient's peritoneal cavity. After a period of time (the "dwell period"), the solution is drained from the patient into a spent solution container.

In IPD, a large amount of solution is cycled in this manner over a relatively short period of time. Once treatment is completed, the patient is unencumbered for at least a few days. A disadvantage is the large amount of dialysis solution that must be utilized. Bags containing 40 liters of solution can be difficult to lift for a patient in a weakened condition.

In CCPD and CAPD methods, the same efficiency of results is obtained by increasing the dwell time of the dialysis solution within the peritoneal cavity. The total amount of solution required can therefore be significantly reduced. The obvious disadvantage, is that there is no "down time" for the treatment.

One of the significant items of expense in peritoneal dialysis of all types is the tubing set. Tubing sets vary widely depending on the type of peritoneal dialysis with which they are used and the brand of cycling equipment with which they are used, but all of them have a cost that is significant, especially when one considers that they are used between several times a week and several times a day for years. Tubing sets must be sterile, and so they are normally used once and then discarded. Thus, for example, a tubing set that costs only ten dollars becomes a fairly major expenditure for a patient that receives dialysis once a day, if that dialysis continues for years as it very often does.

SUMMARY OF THE INVENTION

The present invention includes a tubing set having two main portions: one portion for use in CCPD therapy and another portion for use in CAPD therapy. The two portions are initially in fluid communication with one another and share a single reservoir bag. The CCPD portion includes a set of solution bags in communication with the tubing set through a solution bag manifold, a drain bag and at least one patient connector to connect the tubing set to a patient catheter. The CAPD portion includes a drain bag and a patient connector that is different from the CCPD patient connector.

The tubing set is used by installing it on a cycling machine and operating the cycling machine to pump solution from the solution bags into the reservoir bag for heating, from the heater bag to the patient through the CCPD patient connector, and from the patient into the drain CCPD bag for disposal. In a preferred embodiment, there are two sterile CCPD patient connectors in series with a coupling between them so that one CCPD procedure can be performed by connecting the first of the two patient connectors to the patient catheter and then the patient can be disconnected and the first patient connector can be separated from the tubing set and discarded, and then later a second CCPD procedure can be performed by connecting the second patient connector to the patient catheter. This allows a single tubing set to be used for both an evening procedure and a nighttime procedure, for example.

After the patient has completed the nighttime CCPD portion of the therapy, the patient disconnects from the tubing set. The cycler then automatically fills the reservoir bag with a final dose of solution. The patient then disconnects the CAPD portion of the tubing set from the CCPD portion of the tubing set. The CAPD portion of the tubing set then becomes the mid-day exchange dose and set. The CAPD portion is connected to the patient by connecting the CCPD patient connector to the patient catheter, and the patient is then free to have CAPD therapy without being connected to the cycler machine. The CAPD therapy is accomplished in the traditional manner by flowing solution from the heater bag to the patient, allowing the solution to reside in the patient's peritoneal cavity for a dwell time, and then draining the solution from the patient's peritoneal cavity into the CAPD drain bag.

One aspect of the invention involves recycling the solution bag from a tubing set used in one set of CCPD and CAPD therapies (day 1), into the drain bag used in the CCPD portion of the next set of CCPD and CAPD therapies (day 2). This is done by employing an ordinary CCPD drain bag for the day 1 tubing set used by the patient. The day 2 tubing set, however, does not include its own drain bag; instead, the empty solution bag from the day 1 tubing set is disconnected from the first tubing set and is attached to the day 2 tubing set as the drain bag for the day 2 tubing set. When the user is done with the day 2 tubing set, the day 2 tubing set drain bag (which was the day 1 tubing set solution bag) is discarded along with the rest of the day 2 tubing set, except that the day 2 tubing set empty solution bag is saved and used as the next (day 3) tubing set drain bag, and so on. In this way, all the tubing sets after the first one do not include a drain bag. This saves a considerable amount of bagging material and cost.

BRIEF DESCRIPTION OF THE DRAWINGS

FIG. 4 shows a connector device particularly suited for use with the present invention.

FIG. 4A shows a connector device that is capped which is particularly useful with the present invention.

FIG. 5 shows a tubing coupling particularly suited for use with the present invention.

DETAILED DESCRIPTION OF THE INVENTION

Figure 1:
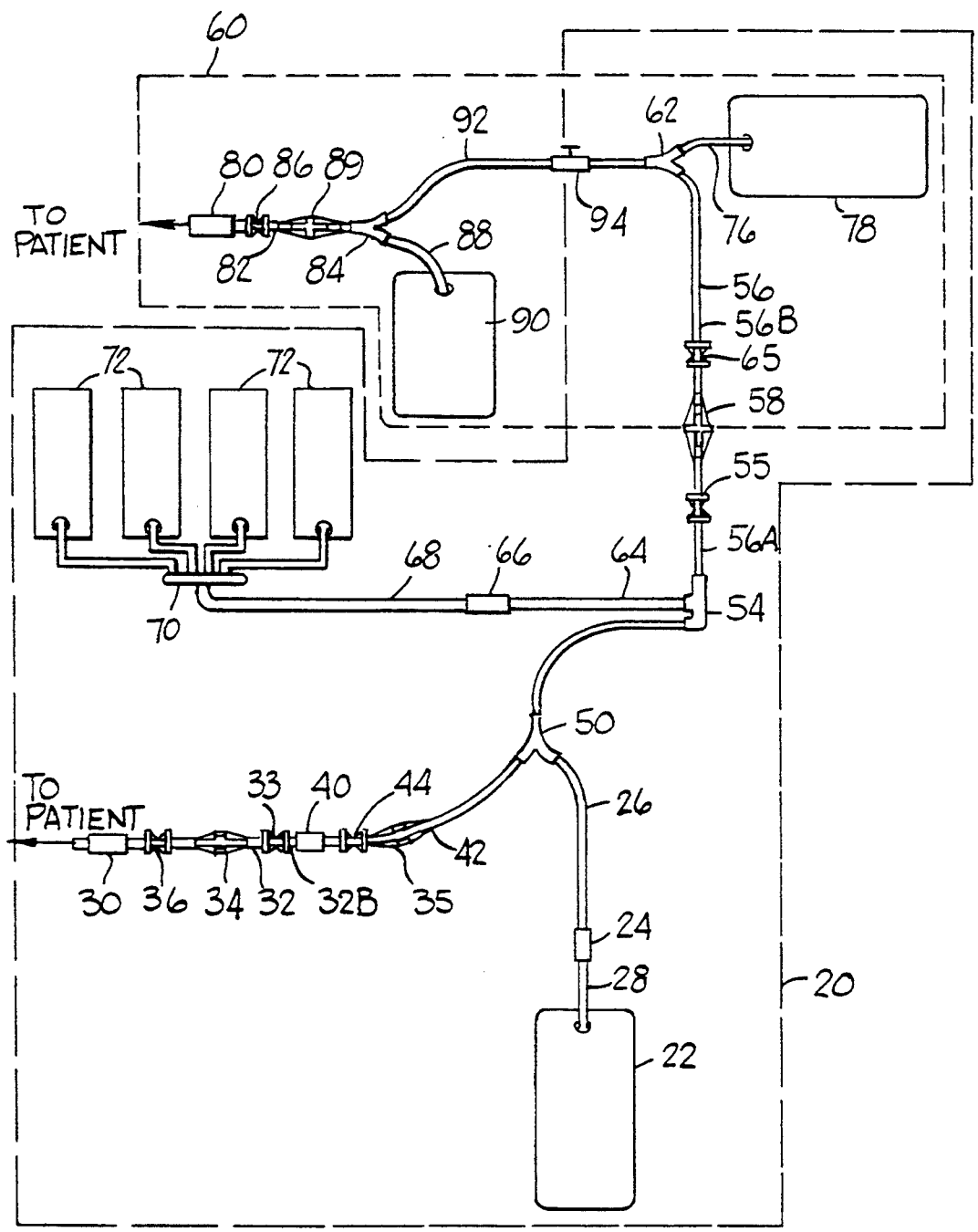
FIG. 1 shows a tubing set in accordance with the present invention.

An overall view of the tubing set 10 of the present invention is shown in FIG. 1. The tubing set 10 includes two main portions which overlap: a CCPD portion 20 and a CAPD portion 60, each of which is enclosed in dotted or dashed lines in FIG. 1. The CCPD portion 20 includes CCPD drain bags 22, a CCPD Y-connector 50, a CCPD drain bag connector 24 and a CCPD drain bag tube 26 which connects the CCPD drain bag connector 24 to one branch of the CCPD Y-connector 50. The CCPD drain bag connector 24 is connected at the opposite end from the CCPD drain bag tube 26 to the CCPD drain bag 22 by a short CCPD drain bag connector tube 28.

A first CCPD patient connector 30 is attachable to a patient catheter (not shown). One end of a CCPD patient connector tubing segment 32 is attached to the first CCPD patient connector 30 on the side of the first CCPD patient connector opposite the patient catheter, and the other end of the CCPD patient connector tubing segment 32 is attached to a second CCPD patient connector 40. The CCPD patient connector tubing segment 32 is comprised of two pieces: 32A which is attached to the first CCPD patient connector 30, and 32B which is attached to the second CCPD patient connector 40. The two pieces 32A and 32B are joined by a CCPD patient connector tubing segment coupling 34. On the CCPD patient connector tubing segment piece 32A which is attached to the first CCPD patient connector 30 is a first CCPD patient connector clamp 36, and on the CCPD patient segment 32B which is attached to the second CCPD patient connector 40 is a clamp 33.

On the side of the second CCPD patient connector 40 opposite the CCPD patient connector tubing segment 32 is a CCPD patient tube 42. One end of the CCPD patient tube 42 is attached to the second CCPD patient connector 40 and the other end of the CCPD patient tube 42 is attached to a branch of the CCPD Y-connector 50. On the CCPD patient tube 42 is a second CCPD patient connector clamp 44 and a second coupling 35. The last branch of the CCPD Y-connector 50 is attached to a CCPD tube 62, and the other end of the CCPD tube 52 is attached to an F-connector 54 (or another Y-connector or some other three-way connector).

The F-connector 54 is connected, through a branch other than the branch connected to the CCPD tube 52, to a CCPD reservoir tube 56. The CCPD reservoir tube 56 comprises two pieces, a first piece 56A with one end attached to the F-connector and an opposite end attached to a CCPD reservoir tube coupling 58, and a second piece 56B with one end attached to the CCPD reservoir tube coupling 58 and an opposite end attached to a reservoir tube Y-connector 62. On the CCPD reservoir tube first piece 56A is a CCPD reservoir tube first clamp 55 and on the CCPD reservoir tube second piece is a CCPD reservoir tube second clamp 65. Connected to a branch of the reservoir tube Y-connector 62 is a reservoir bag tube 76, the other end of which is connected to a reservoir bag 78.

The CAPD tubing set 60 includes a CAPD patient connector 80 having one end connectable to a patient catheter (not shown) and the other end connected to a CAPD patient tube 82. The other end of the CAPD patient tube is connected to a CAPD patient tube Y-connector 84. A CAPD patient tube clamp 86 and a tubing coupling 89 are on the CAPD patient tube 82. Another branch of the CAPD patient tube Y-connector is connected to a CAPD drain tube 88 which runs to a CAPD drain bag 90. The last branch of the CAPD patient tube Y-connector 84 is connected to a CAPD reservoir tube 92. In the CAPD reservoir tube 92 is a valve 94 such as a frangible cone of the type known in the art. The other end of the CAPD reservoir tube 92 is connected to a branch of the reservoir tube Y-connector 62 mentioned above.

The reservoir bag 78 may be called a "heater" bag when used in CCPD therapy, although, it will be apparent that it is not essential that the solution actually be heated in that bag. What is important, and what the claims cover in their references to a "reservoir" bag is a container separate from the solution bags. Further, while various containers are characterized herein as "bags" such as the solution bags, reservoir bag and drain bag, it will be apparent that containers other than bags (such as cartons) may be used without departing from the spirit of the invention.

Figure 2:
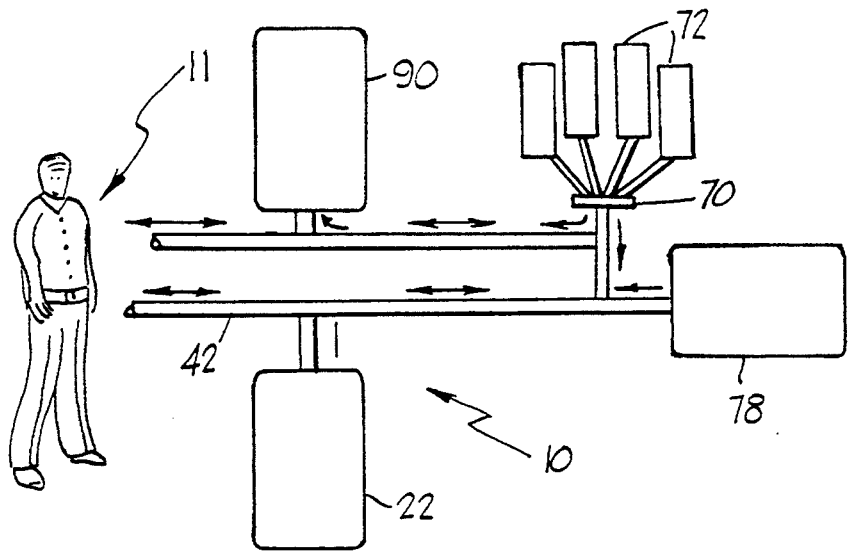
FIG. 2 shows a schematic diagram of the tubing set of the present invention in operation with a peritoneal dialysis cycler.

FIG. 2 shows the tubing set 10 of FIG. 1 in a schematic fashion for attachment to a patient 11 through normal patient catheters. The arrows in FIG. 2 show the direction of solution flow. The valving and connectors are not shown in FIG. 2 for clarity. The solution bags 72 are in fluid communication with the solution manifold 70 which is in fluid communication with the overall tubing set 10. The solution can be pumped from the solution bags 72 through the solution manifold 70 and through the tubing to the reservoir bag 78 in preparation for delivery to the patient. From the reservoir bag 78, the solution can be pumped into the patient through the CCPD patient tube 42 for CCPD therapy. After the dwell time, the solution is out of the patient and into the CCPD drain bag 22. For CAPD therapy, the solution flows from the reservoir bag 78 and through the CAPD patient tube 82. After the CAPD dwell time is completed, the solution flows from the patient into the CAPD drain bag 90.

FIG. 4 shows an example of a connector that can be used in the tubing set to accomplish various connections such as the CCPD drain bag connector 24, the first CCPD patient connector 30, the second CCPD patient connector 40, the solution connector 66 and the CAPD patient connector 80. The connector 110 is of a type known in the art and is described in U.S. patent application Ser. No. 624,142 filed Dec. 7, 1990 and assigned to the assignee of the present invention. Briefly, the connector 110 includes a female portion 114 attached to one tube 116 and a male portion 118 attached to a connecting tube 120. The female portion includes a threaded head 122 which threads into threads 124 in the male portion 118 and a tubular body 130. The male portion 118 includes an inner tube 134 and a concentric outer tube 136. On the inside of the tubular body 130 of the female portion 114 is an inner O-ring seal 140 which seals against the male portion inner tube 134, and on the outside of the tubular body 130 of the female portion 114 is an outer O-ring seal 142 which seals against the male portion outer tube 136. There is a small amount of space 146 between the female portion tubular body 130 and both the inner tube 134 and outer tube 136 of the male portion, which can be filled with a sterilizing agent such as iodine.

FIG. 4A shows the connector 110 with the female portion 114 of FIG. 4 replaced with a cap 150. The cap 150 of FIG. 4A is essentially the same as the female portion 114 of FIG. 4, in having a threaded portion 154 and a tubular body 156 to be received by the male portion 118. However, rather than connecting to the tubing 116 to which the female portion 114 of FIG. 4 connects, the cap simply terminates at the end opposite the male portion 118. The terminating end 160 may include a rigid element 162 for grasping, as shown in FIG. 4A.

The connector having the male portion 118 and cap 150 as shown in FIG. 4A can be used as the first CCPD patient connector 30 and the CAPD patient connector 80 (see FIG. 1) by having the male portion 118 the tubing set so that the cap 150 caps the tubing set. The patient catheter to which the tubing set is connected for performing the dialysis has a female portion 114 which may be capped with a male portion cap. Iodine is in the space between the female portion and male portion of each. When the dialysis is to be performed, the male portion cap is removed from the female portion that is attached to the patient catheter, and the female portion cap is removed from the male portion that is attached to the tubing set. Those two caps are then discarded, and the female portion attached to the patient catheter is joined with the male portion that is attached to the tubing set for a sterile connection.

There are two places in the tubing set using connectors having the female portion attached to one section of tubing and the male portion attached to another section of tubing so that the connector joins the two sections of tubing in a way that allows them to be separated. These places include the solution connector 66 and the drain bag connector 24. At the solution connector 66, the female portion of the connector is attached to the solution tube 68 and the male portion is attached to the solution connecting tube 64. At the drain bag connector 24, the female portion of the connector is attached to the drain bag connector tube 28 and the male portion is attached to the drain bag tube 26. When the new tubing set is put on the cycler to begin a new set of therapies, the solution bag connector 66 is unjoined to remove the old solution bag 72. The new tubing set has a connector with a male portion and a female portion cap at the drain bag connector 24. The female portion cap is removed from the drain bag connector 24, and then the solution bag connector female portion is joined to the drain bag connector male portion, so that the empty solution bag from the old tubing set becomes the drain bag for the new tubing set. The rest of the old tubing set—all of it except the old solution bag—is then discarded.

FIG. 5 shows a tubing coupling of a type known in the art which may be used as the patient connector tubing segment coupling 34 and the heater tube coupling 58. Such a tubing coupling is disclosed in U.S. Pat. No. 5,221,267 assigned to the assignee of the present invention. Briefly, the tubing coupling 210 includes a first tubular portion 242 and a second tubular portion 244, which are separated by an annular ring 250. One or both of the first tubular portion 242 and second tubular portion 244 is scored around its circumference at a scoring line 238 or otherwise weakened. The first tubular portion 242 is inserted into a first tube 230 and the second tubular portion 244 is inserted into a second tube 228 to connect the two tubes and produce fluid communication therebetween. The tubular portions 242 and 244 and the tubes 230 and 228 are preferably sized to result in a secure and watertight fit when the tubular portions are inserted into the tubes. When the tubes 230 and 228 are to be uncoupled, a bending force is applied to the coupling 210. The bending force breaks the tubular portion at the scoring 238 to separate the tubes.

Figure 3:
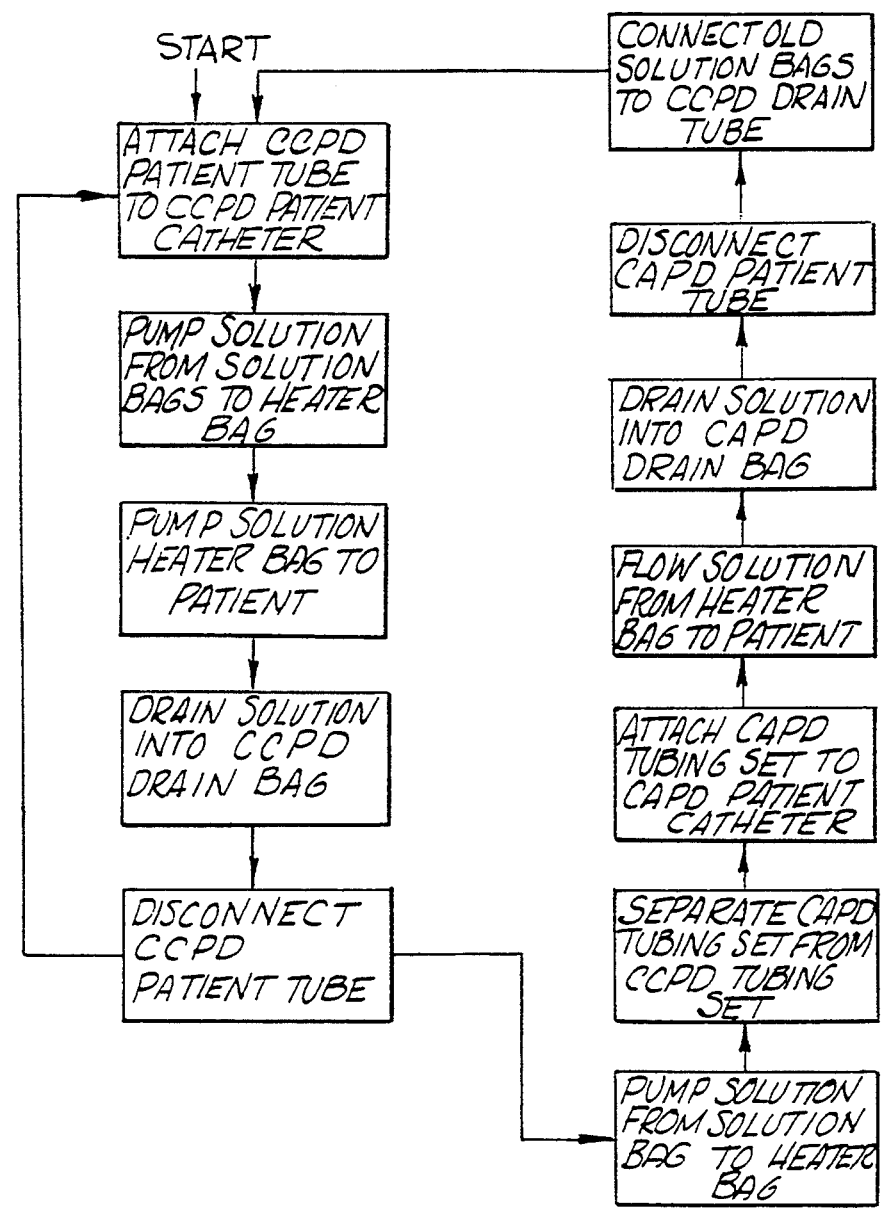
FIG. 3 shows a diagram of the method of operating the tubing set of the present invention.

Next described is the use of the tubing set. The first tubing set used by a patient in the preferred embodiment will include all the elements shown in FIG. 1 including a CCPD drain bag 22. The procedure described below is summarized in the flow chart of FIG. 3. The tubing set is attached to a cycler in a manner well known in the art and dialysis solution is pumped from the solution bags 72 to the reservoir bag 78. The cap to the first CCPD patient connector 30 is removed and the cap to the patient catheter is removed, and the first CCPD patient connector 30 is joined to the patient catheter. Dialysis solution is then pumped into the patient's peritoneal cavity from the reservoir bag 78 for a first CCPD therapy. When the solution dwell time is completed, the solution is pumped from the patient's peritoneal cavity and into the CCPD drain bag 22. During all this time, the clamps 33, 36, 44, 55 and 65 are open. The first patient connector clamp 36 and second patient connector clamp 44 and the clamp 33 are then closed, and the patient connector tubing segment 32 is separated into two pieces 32A and 32B by breaking the patient connector tubing segment coupling 34. The stub of first patient connector 30, patient connector tubing segment piece 32A and clamp 36 is left attached for the patient.

Of course, if the patient's treatment regimen includes only one CCPD procedure rather than two, then only one CCPD patient connector is necessary rather than two. However, if two CCPD procedures are called for, a second CCPD therapy can later be performed by separating the second CCPD patient connector so that the piece 32B of the patient connector tubing segment 32 and half the second CCPD patient connector 40 can be discarded. The stub of first patient connector 30, patient connector tubing segment piece 32A and clamp 36 is removed from the patient by separating the first patient connector 30, and the second CCPD patient catheter 40 is attached to the half of the first patient connector 30 still attached to the patient catheter. Additional dialysis solution is pumped from the solution bags 72 (or the additional solution could have already been pumped from the solution bags 72) to the reservoir bag 78. The second patient connector clamp 44 and clamp 33 are opened, and solution is allowed to flow from the reservoir bag 78 into the patient's peritoneal cavity. After the dwell time is completed, the solution drains back out of the patient's peritoneal cavity and into the CCPD drain bag 22. The second CCPD patient connector clamp 44 and clamp 33 are then closed, and the last patient connector tubing coupling 35 is broken so that a stub of the second patient connector 40 along with a portion of patient tube 42 and attached second patient connector clamp 44 are attached to the patient.

It can be appreciated that this series of CCPD therapies can be more than two in number by simply increasing the number of patient connectors and tubing couplings in series in the patient tube 42. By having three patient connectors on the tube and three tubing couplings, for example, there could be three consecutive CCPD therapies instead of just two, provided that there is sufficient dialysis solution in the solution bags 72.

After the last CCPD treatment is completed, additional solution from the solution bags 72 is pumped to the reservoir bag 78, and the reservoir tube first clamp 55 and second clamp 65 are closed. The reservoir tube 56 is then separated into the first piece 56A and second piece 56B by breaking the reservoir tube coupling 58. The CAPD tubing set 60 is thereby freed from the rest of the tubing set and can be used at the convenience of the patient. The portion of the CCPD tubing set 60 which was separated by breaking the reservoir tube coupling 58 is then discarded, except that the solution bags 72 are saved.

The CAPD tubing set 60 is used as a mid-day CAPD exchange by removing the cap from the patient catheter and removing the cap from the CAPD patient connector 80, connecting the CAPD connector 80 to the patient catheter, draining the existing solution in the patient's peritoneum into the drain bag 90 then opening valve 94 and allowing the solution from bag 78 to flow into the patient's peritoneal cavity, allowing the solution to reside in the peritoneal cavity for a dwell time. The tubing clamp 86 is open during this process. Once the exchange has been made, tubing clamp 86 is closed and the exchange set is separated from the patient by breaking the tubing coupling 89, leaving connector 80 tubing portion 82 and clamp 86 as the cap for the patient catheter connector. The rest of the Y set is discarded. It can be appreciated that in the preferred embodiment described above, the patient always wears a stub of tubing to cap the patient catheter between treatments.

When a second set of therapies is begun, the second tubing set will normally not include a drain bag 22. Instead, the empty solution bags 72 which were saved from the previous tubing set are attached to the new tubing set for use as the drain bag 22. In this manner, it can be seen that the tubing sets save on the cost of a drain bag and reduce the amount of plastic material to be disposed of.

What is claimed is:

1. A peritoneal dialysis tubing set for attachment to a peritoneal cavity connector in fluid communication with a patient's peritoneal cavity, comprising: a set of tubing for CCPD, including a first CCPD patient connector in fluid communication with the CCPD set of tubing for connection to the peritoneal cavity connector, a CCPD drain bag in fluid communication with the CCPD set of tubing, and a solution bag in fluid communication with the CCPD set of tubing and a heating bag in fluid communication with the CCPD set of tubing; including a CAPD patient connector in fluid communication with the peritoneal cavity connector, a CAPD drain bag in fluid communication with the CAPD set of tubing, and a separable tubing connector for detaching the CAPD set of tubing from the CCPD set of tubing when said reservoir bag in fluid communication with the CAPD set of tubing such that the CCPD set of tubing and CAPD set of tubing use the same reservoir bag.

2. The tubing set of claim 1, wherein the CCPD tubing set includes a first at least three-way CCPD connector; a CCPD patient tube having a first end connected to the first CCPD patient connector and a second end opposite the first end connected to said first at least three-way CCPD connector; a CCPD drain tube having a first end connected to the CCPD drain bag and a second end opposite the first end connected to said at least three-way connector; and a CCPD tube having one end attached to the first at least three-way connector and a second end opposite the first end.

3. The tubing set of claim 2, wherein the CAPD tubing set includes a first at least three-way CAPD connector; a CAPD patient tube having a first end connected to the CAPD patient connector and a second end opposite the first end connected to said first at least three-way CAPD connector; a CAPD drain tube having a first end attached to said CAPD drain bag and a second end opposite the first end attached to the first at least three-way CAPD connector; and a CAPD tube having a first end attached to said first at least three-way CAPD connector and a second end opposite the first end in fluid communication with the reservoir bag.

4. The tubing set of claim 3, wherein the CCPD tubing set includes a second at least three-way CCPD connector, the second end of the CCPD tube being connected to the second at least three-way CCPD connector; a solution tube having a first end attached to the second at least three-way CCPD connector and a second end opposite the first end attached to the solution bag; and a CCPD reservoir tube having one end attached to said second at least three-way CCPD connector and a second end opposite the first end in fluid communication with the reservoir bag.

5. The tubing set of claim 4, wherein the CAPD tubing set includes a second at least three-way CAPD connector, the second end of the CAPD connector and the second end of the CCPD reservoir tube being attached to the second at least three-way CAPD connector; a CAPD reservoir tube having a first end attached to a CAPD reservoir tube and a second end opposite the first end attached to said second at least three-way CAPD connector.

6. The tubing set of claim 5 wherein the separable tubing coupling is in the CCPD reservoir tube.

7. The tubing set of claim 6, wherein the CCPD reservoir tube includes at least two first pieces of tubing, and the separable tubing coupling includes a tubular member insertable into one piece and a second tubular member opposite the first tubular member insertable into the other piece to establish fluid communication between the two pieces; at least one tubular member being scored to be breakable along the scoring to separate the two pieces.

8. The tubing set of claim 7, wherein the tubing coupling includes an annular ring between the first tubular element and second tubular element and second tubular element are insertable into the two pieces.

9. The tubing set of claim 2, wherein the CCPD patient tube includes a second CCPD patient connector for connection to the peritoneal cavity connector, and a separable patient tube connector between the first CCPD patient connector and second CCPD patient connector.

10. The tubing set of claim 2, wherein the CCPD drain tube includes two pieces and a CCPD drain tube connector releasably connecting the two pieces; and further comprising a solution tube for establishing said fluid communication between the solution bag and the CCPD set of tubing, the solution tube including two pieces and a solution tube connector releasably connecting the two pieces, the drain bag connector and solution tube connector being such that solution drain bag can be disconnected at the drain bag connector and the solution bag can be disconnected at the solution tube connector and then the solution bag can be attached to the drain bag connector.

11. A method of peritoneal dialysis, comprising attaching to a connector in fluid communication with a patient's peritoneal cavity, a tubing set including a set of tubing for CCPD and a set of tubing for CAPD and a separable tubing coupling for detaching the CAPD set of tubing from the CCPD set of tubing; administering CCPD therapy to the patient; detaching the CAPD set of tubing from the CCPD set of tubing; and administering CAPD therapy.

12. The method of claim 11, wherein the CCPD set of tubing and the CAPD set of tubing share a common reservoir bag.

13. The method of claim 12, wherein the CCPD set of tubing and the CAPD set of tubing share a common solution bag.

14. The method of claim 11, wherein the tubing coupling includes a scored tubular element that is breakable at the scoring, and said step of detaching the CAPD set of tubing from the CCPD set of tubing is by breaking the tubing coupling at the scoring.

15. The method of claim 11, wherein said step of administering CCPD therapy includes pumping dialysis solution from a solution bag to a reservoir bag and then pumping said dialysis solution from the reservoir bag to the patient.

16. The method of claim 15, wherein said step of administering CAPD therapy includes pumping dialysis solution from said solution bag to said reservoir bag and transferring said dialysis solution from the reservoir bag to the patient.

17. The method of claim 11, wherein said step of administering CCPD therapy includes at least two CCPD therapies, the tubing set being connected to the patient for a first CCPD therapy by a first CCPD connector on the CCPD set of tubing, and the tubing set being connected to the patient for a second CCPD therapy by a second CCPD connector on the CCPD set of tubing.

18. The method of claim 17, wherein the CCPD tubing set includes a patient tube having the first CCPD patient connector and second CCPD connector and a separable tubing coupling therebetween; and said step of administering CCPD therapy includes separating the first CCPD patient connector from the tubing set after the first CCPD therapy by separating said tubing coupling.

19. The method of claim 11, further comprising completing said peritoneal dialysis; disconnecting an empty solution bag from said tubing set; and attaching said empty solution bag to a new tubing set to act as a drain bag in the new tubing.

* * * * *